(12) United States Patent
Wieczorek et al.

(10) Patent No.: US 9,012,856 B2
(45) Date of Patent: Apr. 21, 2015

(54) GANTRY-FREE SPECT SYSTEM

(71) Applicant: Koninklijke Philips N.V., Eindhoven (NL)

(72) Inventors: Herfried Karl Wieczorek, Aachen (DE); Jinghan Ye, Cupertino, CA (US); Lingxiong Shao, Saratoga, CA (US); Rizwan Hassan, Danville, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/357,597

(22) PCT Filed: Nov. 12, 2012

(86) PCT No.: PCT/IB2012/056343
§ 371 (c)(1),
(2) Date: May 13, 2014

(87) PCT Pub. No.: WO2013/076614
PCT Pub. Date: May 30, 2013

(65) Prior Publication Data
US 2014/0319360 A1    Oct. 30, 2014

Related U.S. Application Data

(60) Provisional application No. 61/562,593, filed on Nov. 22, 2011.

(51) Int. Cl.
G01T 1/20    (2006.01)
G01T 1/29    (2006.01)
A61B 6/03    (2006.01)
G01T 1/164    (2006.01)
A61B 6/00    (2006.01)

(52) U.S. Cl.
CPC .............. *G01T 1/2985* (2013.01); *A61B 6/037* (2013.01); *G01T 1/1648* (2013.01); *A61B 6/4258* (2013.01); *A61B 6/469* (2013.01); *A61B 6/506* (2013.01)

(58) Field of Classification Search
CPC ........................................................ G01T 1/20
USPC ........................................... 250/362, 363.04
See application file for complete search history.

(56) References Cited

U.S. PATENT DOCUMENTS 8,748,826 B2 *    6/2014    Rousso et al. ........... 250/363.04
2004/0251419 A1    12/2004    Nelson et al.

* cited by examiner

Primary Examiner — David Porta
Assistant Examiner — Faye Boosalis

(57) ABSTRACT

A gantry free nuclear imaging system (10) images a region of interest (ROI) (16). The system (10) includes one or more radiation detectors (20) generating radiation data indicating the location of gamma photon strikes. The system includes a reconfigurable frame (22) positioning the radiation detectors (20) at fixed viewing angles of the ROI (16) and at least one processor (44, 48). The processor (44, 48) receives the radiation data from the radiation detectors (20) and reconstructs an image of the ROI (16) from the received radiation data.

18 Claims, 5 Drawing Sheets

GANTRY-FREE SPECT SYSTEM

CROSS REFERENCE TO RELATED APPLICATIONS

This application is a national filing of PCT application Serial No. PCT/IB2012/056343, filed Nov. 12, 2012, published as WO 2013/076614 A1 on May 30, 2013, which claims the benefit of U.S. provisional application Ser. No. 61/562,593 filed Nov. 22, 2011, which is incorporated herein by reference.

The present application relates generally to nuclear medical imaging. It finds particular application in conjunction with single-photon emission computed tomography (SPECT) and will be described with particular reference thereto. However, it is to be understood that it also finds application in other usage scenarios and is not necessarily limited to the aforementioned application.

SPECT is a nuclear medical imaging technique that employs a radioisotope injected into a patient to image a region of interest (ROI) of the patient. Typically, the radioisotope is combined with a radioligand to create a radiopharmaceutical that binds to specific types of tissue. The radioisotope undergoes gamma-ray decay at a predictable rate and characteristic energy. One or more radiation detectors are placed adjacent to the patient to monitor and record emitted radiation. Typically, the radiation detectors are Anger cameras.

An Anger camera typically includes one or more photomultiplier tubes affixed to the rear of one or more flat scintillation elements, such as sodium iodide crystals. The scintillation elements generate light flashes when struck by gamma photons and the photomultipliers detect the location and intensity of the light flashes. Further, the Anger camera typically includes one or more collimators controlling the direction and angular spread from which each scintillator element can receive radiation. Such radiation detectors provide a two-dimensional image of radiation distribution.

To obtain a three-dimensional image, the radiation detectors are rotated or indexed around the patient to monitor the emitted radiation from a plurality of angles, thereby creating a plurality of two-dimensional images of radiation distributions at different angles. Suitably, a gantry is employed to support and move the radiation detectors around the patient. Using the created two-dimensional images and the corresponding angles, a three-dimensional image is reconstructed.

Challenges with employing traditional SPECT systems follow from the radiation detectors, which are bulky and heavy. The radiation detectors require stable, expensive gantries that limit mobility. Additional challenges follow from the collimators typically employed by SPECT systems. Typically, SPECT systems employ parallel-hole collimators and/or modifications thereof, such as fan-beam collimators. Such collimation principles require a rotating gantry and at least one detector, typically two, to obtain the necessary number of viewing angles for reconstruction, which further limits mobility and adds cost.

The present application provides a new and improved system which overcomes the above-referenced problems and others.

In accordance with one aspect, a nuclear imaging system images a region of interest (ROI). The system includes one or more radiation detectors generating radiation data indicating the location of gamma photon strikes. Further, the system includes a frame positioning the radiation detectors at fixed viewing angles of the ROI and at least one processor. The processor receives the radiation data from the radiation detectors and reconstructs an image of the ROI from the received radiation data.

In accordance with another aspect, a method images a region of interest (ROI). A frame is selected for the geometry of the ROI and the frame is arranged relative to the ROI to position one or more radiation detectors at fixed viewing angles of the ROI. The radiation detectors generate radiation data indicating the location of gamma photon strikes. The radiation data from the radiation detectors is collected by at least one processor and an image of the ROI is reconstructed by the processor from the received radiation data.

One advantage resides in a mobile and versatile system for near-field organ-focused imaging.

Another advantage resides in improved spatial resolution.

Another advantage resides in improved system sensitivity.

Another advantage resides easy patient access and imaging during interventions.

Another advantage resides in dynamic imaging.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The present disclosure provides a single-photon emission computed tomography (SPECT) system that does not need a stationary or rotating gantry. Instead, the system employs detector modules arranged in frames. The system is particularly well suited for applications such as imaging the heart, brain, thyroid, bones, joints, ligaments, tendons, muscles, nerves, kidneys, lungs, and the like. Before imaging, a frame is chosen according to the geometry of the region of interest (ROI) and positioned over and/or around the ROI. A frame may be common to a plurality of applications, such as brain and cardiac applications, or application specific. Further, the position of detector modules and/or frames is suitably static during imaging.

In some embodiments, selected frame is configurable to the target application. For example, the selected frame can be configured in the shape of a circle or ellipse for brain imaging. Other shapes include ellipses, partial circles or ellipses, and so on. A reconfigurable frame is suitably formed of a plurality of subframes pivotally connected to each other like a chain. The subframes typically share a common size and/or shape, but different sized subframes are contemplated. Different shapes include, for example, squares and rectangles.

In embodiments employing subframes, the frame is configured by pivoting subframes to the desired position. Then the positions of the subframes relative to one another are fixed, for example, with a locking and/or braking mechanism. The subframes can be pivotally arranged into the desired position manually and/or automatically. As to the latter, motors and/or actuators or the like can be employed. The shape of the frame can also be adjusted by adding and/or removing subframes to the frame. For example, where the ROI is small, subframes can be removed from a frame. As another example, where the ROI is large, additional subframes can be added to the frame.

After achieving the desired shape, the angular relationship of adjacent subframes is determined. This can be determined manually, but is typically determined automatically. In embodiments determining the angular relationship of adjacent subframes automatically, resolvers can be employed. Additionally or alternatively electrical transponders or fiducials on the frame can be employed.

Figure 1:
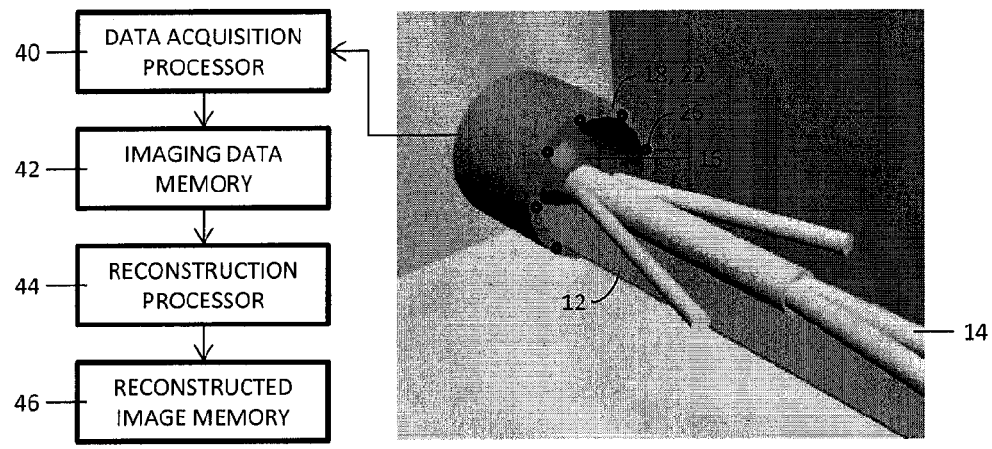
FIG. 1 illustrates a gantry-free SPECT system with a frame positioning radiation detectors around a patient's brain.
Figure 2:
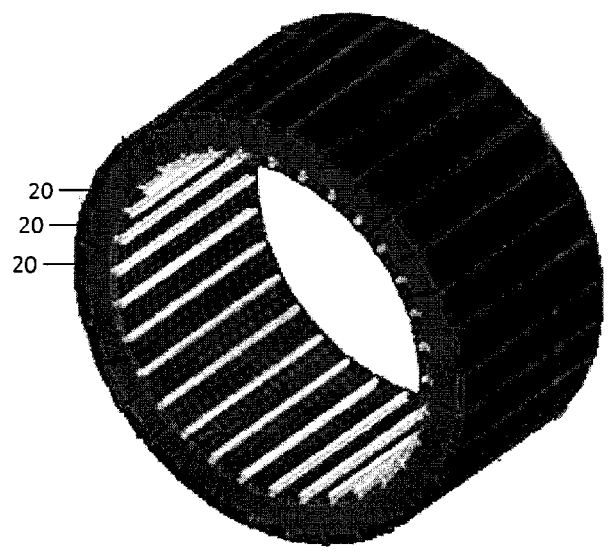
FIG. 2 illustrates the frame of FIG. 1.
Figure 3:
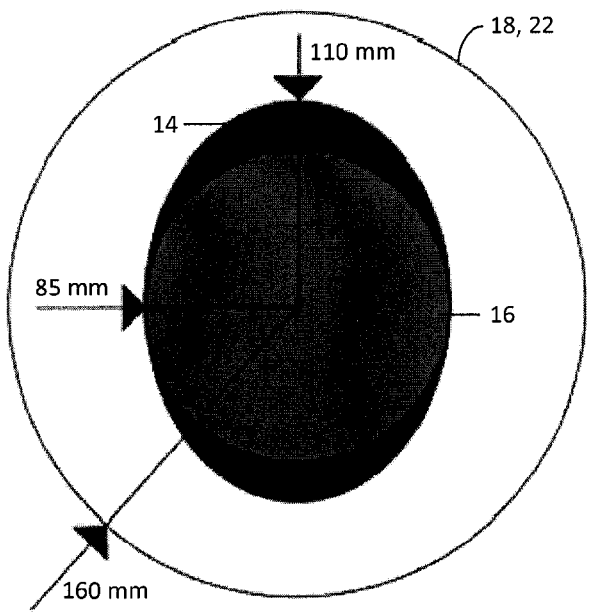
FIG. 3 illustrates the positioning of the frame of FIG. 1 around the patient's brain.

With reference to FIGS. 1-3, a SPECT system 10 includes a patient support 12, such as a patient bed, to support a patient 14. The patient 14 includes a ROI 16 to be imaged by the system 10. Examples of the ROI 16 include, but are not limited to, hearts, brains, thyroids, bones, joints, ligaments, tendons, muscles, nerves, kidneys, lungs, tumors, lesions, and so on. Before imaging, the ROI 16 is injected with one or more radioisotopes, and the patient 14 is placed on the patient support 12. Examples of such radioisotopes include, but are not limited to, Tc-99m, I-131, Ga-67, and In-111. In some embodiments, the radioisotopes are combined with radioligands to create a radiopharceutical that binds to or is preferentially absorbed by specific types of tissue.

Figure 4:
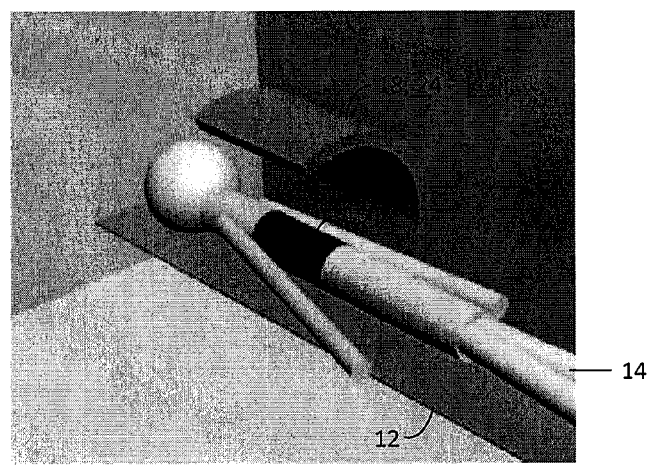
FIG. 4 illustrates the frame positioning the radiation detectors around a patient's heart.
Figure 5:
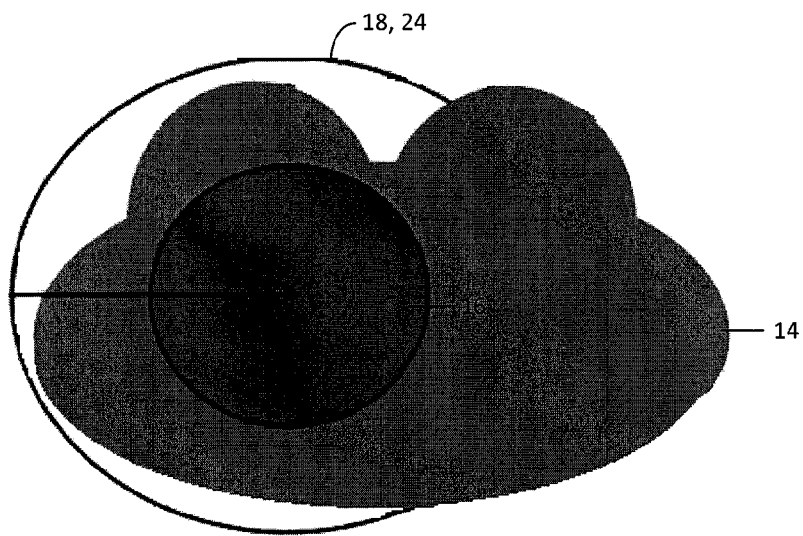
FIG. 5 illustrates the positioning of the frame of FIG. 4 around the patient's heart.

One or more subframes 18 of the system 10 support one or more radiation detectors 20 of the system 10 (see FIG. 2) for detecting radiation events and imaging the ROI 16, as discussed hereafter. Further, the subframes 18 typically position the radiation detectors 20 at different viewing angles of the ROI 16 to allow image reconstruction. For example, as illustrated, the ROI 16 is the brain of the patient 14 and a frame 22 of the subframes 18 arranges the radiation detectors 20 in a ring (e.g., 192 mm wide and 1024 mm long) around the brain of the patient 14. As another example, with reference to FIGS. 4 and 5, the ROI 16 is the heart and another frame 24 of the subframes 18 or the frame 22 in a reconfigured state arranges the radiation detectors 20 in a partial ring around the heart of the patient 14.

Referring back to FIGS. 1-3, each subframe can be employed for one or more applications. For example, a broad belt frame of detector modules can be employed for the brain imaging, and a longer, thinner belt frame can be employed for whole body imaging. In some embodiments, a frame is specifically designed for one or more applications. In other embodiments, a frame can be manipulated or bent as necessary and/or resized (e.g., by adding subframes) for a specific application.

In one example, the subframes 18 are rectangular elements that are pivotally connected to each other like a chain. When the subframes 18 are pivoted to a selected location, the position is fixed with a lock or brake. Resolvers can measure the angular relationship of adjacent subframes. In another embodiments, motors are controlled to set the configuration of the subframes 18. In another embodiment, the subframes 18 are connected by connectors with fixed angular orientations defined by the connectors.

Figure 6:
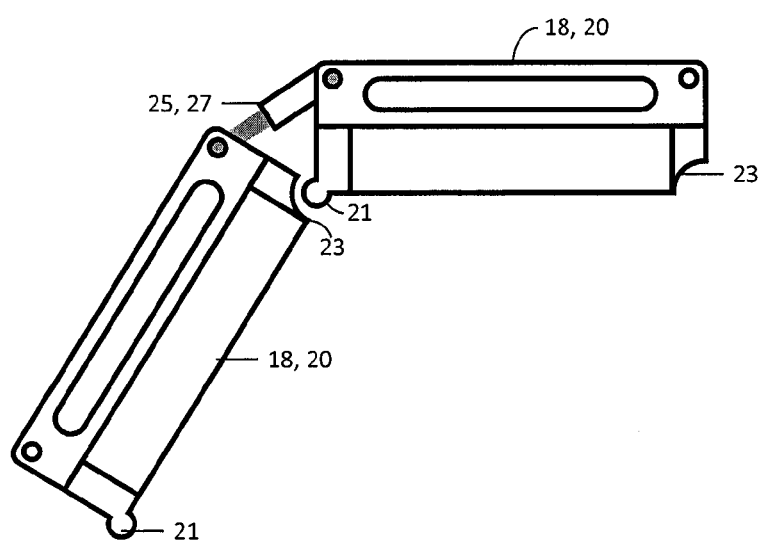
FIG. 6 illustrates an example of a configurable frame.

In another one example, shown in FIG. 6, the detectors 20 include at least two detectors and the subframes 18 are part of the detector edges. The two opposite sides of the detector edges have a minimum of two spherical indexes 21 and two magnet receptors 23 on the opposite side allowing the two detectors to couple. The spherical indexes 21 and the magnet receptors 23 when coupled to each other allow angular manipulation and disconnection for storage of the two detectors. An adjustable tie-rod 25 maintains the angular shape of the two detectors which is also removable. The tie-rod 25 can also be a motor driven by an actuator 27 that adjusts the angular shape of the detectors 20 based on a selected clinical protocol.

The viewing angle of the radiation detectors 20 can be determined from the shape, and the location and orientation, of the frame relative to the ROI 16 using well known techniques. The location and orientation of a frame can be determined, using for example, electrical transponders or fiducials on the frame or specified by an operator of the system 10 using a user input device.

The shape of a frame can be automatically determined and/or manually specified. As to the former, the frame can include one or more sensors 26 generating data to identify the shape of the frame. For example, electromagnetic transponders can be placed on the frame (e.g., between each subframe). As another example, optical fibers can be placed along the length frame and the fiber Bragg grating (FBG) principle can be used to determine the shape of the fibers, and hence the frame. As to the latter, an operator of the system 10 can specify the shape of a frame with a user input device. Typically, the automatic approach is employed for frames that can be manipulated or bent, whereas the manual approach is typically employed for frames that are specifically designed for an application.

Before imaging, a frame is typically selected for the ROI 16 and arranged, with the patient support 12, so the frame is positioned over and/or around the ROI 16. It is contemplated that frames that aren't in use are stored in the apron of the patient support 12. Typically, to position the frame over and/or around the ROI 16, the frame is mounted to the patient support 12. However, other mount points, such as walls, ceilings, stands, and so on are contemplated. Insofar as the frame is mounted to the patient support 12, the frame can suitably be mounted at varying locations along the periphery of the patient support 12 to allow the imaging of different ROIs. In some embodiments, this is facilitated by tracks along the length of the patient support that interlock with the frame and only allow the frame to selectively move along the length of the patient support 12.

During imaging, the subframes 18 and/or the patient support 12 are typically static. No rotating gantry or moving patient support is required. However, it is contemplated that the subframes 18 and/or the patient support 12 can pivot slightly and/or move during imaging. For example, the patient can be moved laterally and/or vertically relative to the radiation detectors 20 slightly during imaging and/or the radiation detectors 20 can be moved laterally and/or vertically relative to the patient support 12 slightly during imaging. Because the subframes 18 typically remain static during imaging, the subframes 18 support, and the radiation detectors 20 include, a sufficient number of radiation detectors to capture all the viewing angles of the ROI 16 for image reconstruction. This will depend upon the ROI 16 and the image reconstruction algorithm. Advantageously, the use of frames rather than a gantry reduces cost for certain applications and improves mobility of the system 10.

The radiation detectors 20 receive gamma photons emitted by the radioisotopes injected into the ROI 16 and generate radiation data indicating the location of the radioisotopes within the ROI 16. In some embodiments, the radiation detectors 20 are modular and share the same size and area (e.g., 32 mm×32 mm) to allow the radiation detectors 20 to be moved from one frame to another. For example, the radiation detectors 20 can be used for a frame designed for cardiac imaging and for a frame designed for brain imaging by mounting the radiation detectors 20 to the frames. To secure the radiation detectors 20 to the subframes 18, any approach of removably connecting the radiation detectors 20 is appropriate. For example, the frames 20 can include tracks for slidingly receiving the radiation detectors 20 and holding the radiation detectors 20 on two sides.

Figure 7:
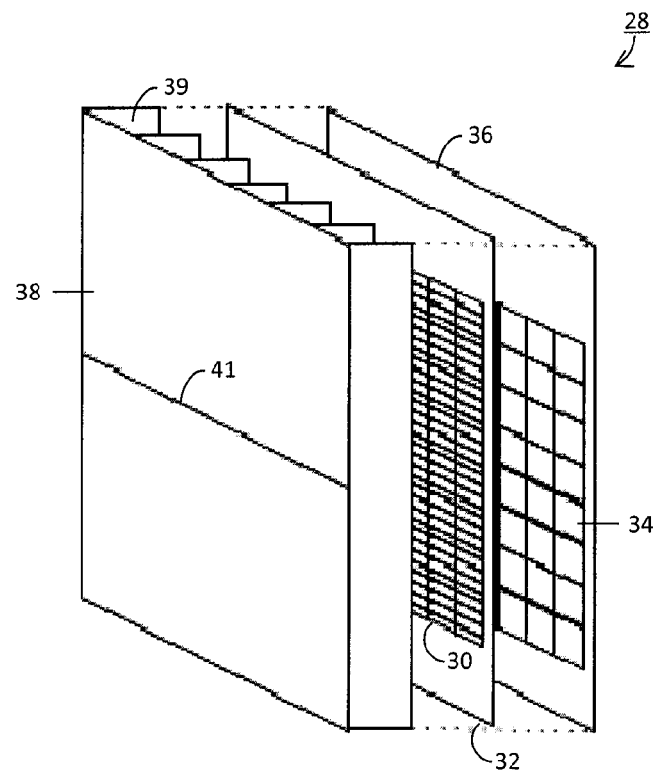
FIG. 7 illustrates one configuration of a radiation detector.
Figure 8:
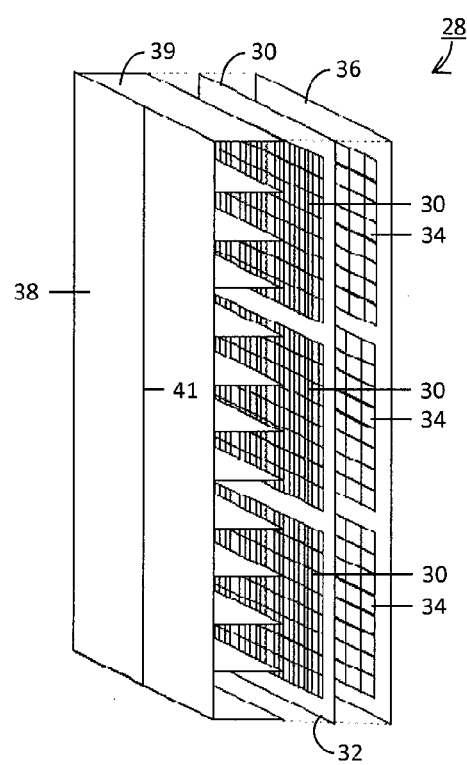
FIG. 8 illustrates another configuration of the radiation detector of FIG. 6.

With reference to FIGS. 7 and 8, in some embodiments, a radiation detector 28 includes one or more scintillator elements 30 generating light flashes when struck by gamma photons. The location of a light flash corresponds to the location of a gamma photon strike. In some embodiments, the scintillator elements 30 are pixelated, typically with 1×4 mm pixels. Further, in some embodiments, the scintillation elements 30 include a receiving face 32 which receives the gamma photons emitted by the radioisotopes. When the receiving face 32 receives a gamma photon, the scintillation elements 30 emit a light flash at least partially from an output face (not shown) of the scintillation elements 30, opposite the receiving face 32. Examples of scintillation elements include scintillator plates, individual scintillation crystals (e.g., sodium iodide crystals), and the like. In some embodiments, the scintillator elements 30 are pixelated.

One or more light sensitive elements 34 sense the light flashes generated by the scintillator elements 30 and generate radiation data indicating the location and intensity of the light flashes. In some embodiments, the light sensitive elements 34 are pixelated, typically with 4×4 mm pixels. Notably, the pixels of the light sensitive elements 34 are typically larger than pixels of the scintillator elements 30 and Anger logic is employed for positioning the scintillator elements 30. Further, in some embodiments, the light sensitive elements 34 include a receiving face 36 which receives the light flashes emitted by the scintillation elements 30. In such embodiments, the output face and the receiving face 36 of the light sensitive elements 34 are spatially correlated optically. The light sensitive elements 34 then sense the location of light flashes by sensing the location of light flashes striking the receiving face 36 of the light sensitive elements 34. Since the receiving face 36 of the light sensitive elements 34 are spatially correlated optically, locations on the receiving face 36 of the light sensitive elements 34 can be correlated with locations on the output face, which correspond to locations on the receiving face 32 of the scintillator elements 30.

Any approach for spatially correlating the output face and the receiving face 36 of the light sensitive elements 34 optically is contemplated. However, suitably this is performed by positioning the receiving face 36 of the light sensitive elements 34 proximate to and/or abutting the output face. Other approaches include the use of a light guide, such as a plurality of light pipes, to transport light from the output face to the receiving face 36 of the light sensitive elements 34. Light pipes include, for example, optical fibers. Anger logic can be used to localize the scintillations.

In one embodiment, the light sensitive elements 34 include digital or analog silicon photomultipliers (SiPMs). While analog SiPMs are amenable to the present disclosure, suitably digital SiPMs are employed. Pixelated scintillator elements, in one embodiment, are coupled 1:1 with the SiPMs. It is also contemplated that the light sensitive elements 34 can employ photomultiplier tubes, photodiodes, opto-electric transducers, direct photon to electrical converters (a.k.a., semiconductor gamma detectors), such as semiconductor crystals, zinc-cadmium telluride (CZT) elements, and the like, and so on.

Each radiation detector further includes one or more collimators 38 controlling the direction and angular spread from which each scintillator element of the radiation detector can receive radiation. In other words, the collimators 38 ensure the scintillator elements 30 receive radiation along known rays or trajectories. Typically, the collimators 38 include one or more openings limiting the radiation received by the scintillator elements to the radiation that passes through the openings. Examples of collimators include pin-hole, slat-slit and fan beam-slit.

In a pin-hole or slat-slit collimator, the pin-hole or slat-slit functions analogous to a pin-hole camera to focus the radiation on the scintillator elements or solid state detector array. In the slat-slit camera, the slats 39 limit the spread or divergence of the radiation trajectories in the direction of the slit 41.

In some embodiments, a plurality of the light sensitive elements 34, for example, six in a row, share a slat-slit or fan beam-slit collimator. Further, in some embodiments, the collimators 38 are modular to allow the system 10 to be employed for different imaging techniques. For example, collimators for SPECT imaging or planar imaging can be employed depending upon the desired imaging technique. In embodiments employing modular collimators, the collimators 38 can be secured to their respective radiation detectors using, for example, mechanical fasteners or a system of interlocking grooves.

In the embodiment of FIG. 7, the radiation detector 28 includes a single light sensitive element array, such as a digital SiPM array, and a single scintillator element, such as a plate of sodium iodide crystals. Further, a single slat-slit collimator is employed to control the direction and angular spread of gamma photons hitting the scintillator element. In the embodiment of FIG. 8, the radiation detector 28 includes a single scintillator element and three light sensitive element arrays in a row.

Referring back to FIGS. 1-3, a data acquisition processor 40 of the system 10 collects radiation data from each of the radiation detectors 20 for a predetermined period of time. For each of the radiation detectors 20, the radiation data typically includes energy of gamma photon strikes and the corresponding locations of the gamma photon strikes. In some embodiments, for each radiation detector, the data acquisition processor 40 uses the radiation data to generate a radiation distribution over the spatial range of the radiation detector.

The data acquisition processor 40 further receives and/or determines the angular position of each radiation detector relative to the ROI 16 and correlates the angular positions with the received radiation data and/or radiation distributions. In some embodiments, the angular positions of the radiation detectors are received from the radiation detectors 20 or other components of the system 10. In other embodiments, the angular positions are determined from the shape, and the location and orientation, of the frame relative to the ROI 16, as discussed above.

The radiation data and/or the radiation distributions are stored in an imaging 42 memory of the system 10. Further, the angular positions of the radiations, correlated with the radiation data and/or radiation distributions, are further stored in the imaging memory 42. A reconstruction processor 44 of the system 10 processes the data from the imaging data memory 42 into a three-dimensional image representation. In some embodiments, this includes generating a radiation distribution over the spatial range of each radiation detector from the radiation data. The image representation is stored in a reconstruction image memory 46 of the system 10 for subsequent use. For example, the three-dimensional image can be employed by a video processor and/or displayed on a display.

Although not described in detail, those skilled in the art will appreciate that the system 10 can be modified for positron emission tomography (PET) imaging by removing the collimators and adjusting the reconstruction algorithm. Applications for such PET imaging include dosimetry control during proton therapy. Further, the system 10, whether employed for SPECT or PET imaging, can be combined with computed tomography (CT), volume imaging (XCT), or magnetic resonance (MR) for multimodal imaging by using just one patient support for both applications.

Figure 9:
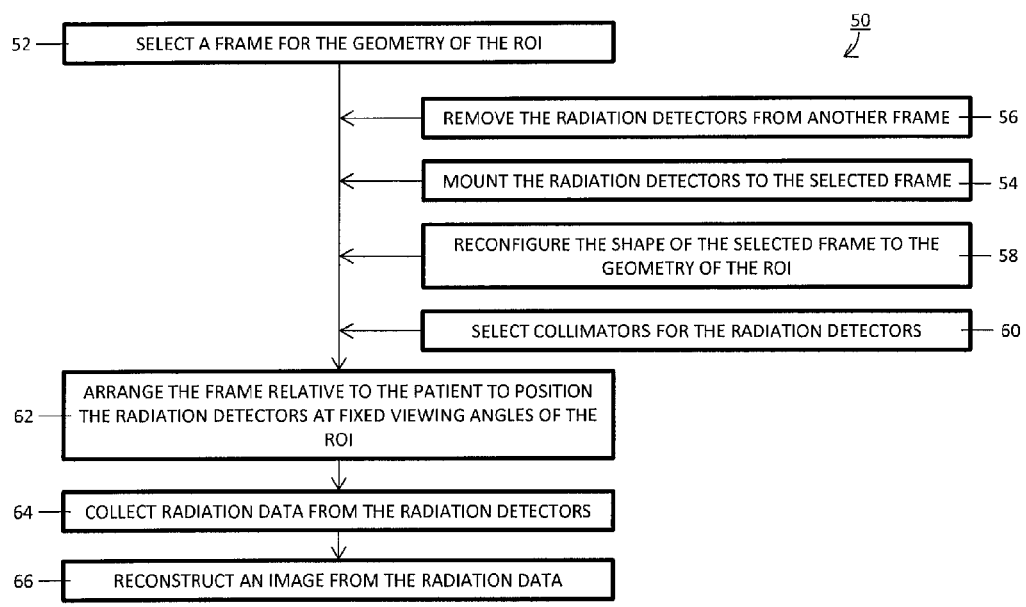
FIG. 9 illustrates a block diagram of a method of imaging a patient using the gantry-free SPECT system of FIG. 1.

With reference to FIG. 9, a method 50 for imaging the ROI 16 is provided. Suitably, the method 50 is performed by an operator of the system 10 with the aid of at least one processor, such as the data acquisition processor 40 and/or the reconstruction processor 44, executing computer executable instructions stored on a memory, such as the imaging memory 42 and/or the reconstructed image memory 46. The method 50 includes selecting 52 a frame for the geometry of the ROI 16.

In some embodiments, after selecting 52 the frame, the radiation detectors 20 are mounted 54 to the frame. For example, the radiation detectors 20 are secured to the frame with tracks in the frame. Further, in some embodiments, the radiation detectors mounted 54 to the frame are first removed 56 from another one of the frames. Even more, in some embodiments, the shape of the selected frame is reconfigured 58 to the geometry of the ROI 16 and/or collimators for the radiation detectors 20 are selected 60 based on an imaging technique used for image reconstruction.

The frame is further arranged 62 relative to the patient 14 to position the radiation detectors 20 at fixed viewing angles of the ROI 16. The radiation detectors, as noted above, 20 generate radiation data indicating the location of gamma photon strikes. Once the frame is arranged 62, the radiation data is collected 64 by at least one processor from the radiation detectors 20 and an image of the ROI 16 is reconstructed 66 by the processor from the received radiation data.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; and a user input device includes one or more of a mouse, a keyboard, a touch screen display, one or more buttons, one or more switches, one or more toggles, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A gantry free nuclear imaging system for imaging a region of interest (ROI), said system comprising:
   one or more radiation detectors generating radiation data indicating the location of gamma photon strikes;
   a frame positioning the radiation detectors at fixed viewing angles of the ROI, the frame formed from pivotally connected subframes supporting the radiation detectors;
   at least one processor programmed to:
      receive the radiation data from the radiation detectors; and
      reconstruct an image of the ROI from the received radiation data;
   wherein the radiation detectors are modular and movable between subframes.

2. The system according to claim 1, wherein the frame is configured for the geometry of the ROI, said configuration achieved by manual adjustment of tie-rods of the frame and/or activation of one or more actuators of the frame by user selected clinical protocols.

3. The system according to claim 1, wherein at the pivotal connection, the subframes include at least one spherical index element received in a magnetic receptor.

4. A gantry free nuclear imaging system for imaging a region of interest (ROI), said system comprising:
   a plurality of radiation detectors configured to generate radiation data indicating the location of a gamma photon received from the ROI;
   a plurality of pivotally connected subframes configured to receive and support the radiation detectors, the subframes being selectively configured in at least a circle, an ellipse, and a partial circle by pivoting the subframes around the pivotal connections to define a ROI of a selected shape and size;
   a means for determining an angular orientation of each subframe relative to each adjacent subframe; and
   at least one processor programmed to:
      receive the radiation data from the radiation detectors; and
      reconstruct an image of the ROI from the received radiation data.

5. The system according to claim 4, wherein the means for determining the angular orientation includes resolvers configured to measure an angular relationship between adjacent subframes.

6. The system according to claim 4, wherein the means for determining the angular orientation includes at least one of transponders and fiducials mounted to the subframes.

7. The system according to claim 4, wherein the means for determining the angular orientation includes at least one of optical fibers using a fiber Bragg grating principle.

8. A gantry free nuclear imaging system for imaging a region of interest (ROI), said system comprising:
   radiation detectors generating radiation data indicating the location of gamma photon strikes;
   a frame positioning the radiation detectors at fixed viewing angles of the ROI, the frame including a sensor configured to determine the shape of the frame and viewing angles of the radiation detectors;
   at least one processor programmed to:
      receive the radiation data from the radiation detectors; and
      reconstruct an image of the ROI from the received radiation data.

9. The system according to claim 8, wherein a shape of the frame is reconfigurable to the geometry of the patient's ROI.

10. The system according to claim 8, wherein the radiation detectors are modular and movable between frames.

11. The system according to claim 8, wherein each radiation detector includes:
   a collimator controlling the direction and angular spread of gamma photons striking one or more scintillator elements or one or more light sensitive elements.

12. The system according to claim 11, wherein the collimator is one of a pin-hole collimator, a slat-slit collimator and a fan beam-slit collimator.

13. The system according to claim 8, wherein at least one of the radiation detectors includes:
- a scintillator element generating light flashes in response to gamma photon strikes; and
- a light sensitive element, such as a digital silicon photomultiplier, generating radiation data in response to the light flashes.

14. A method for imaging a region of interest (ROI), said method comprising:
- reconfiguring a shape of a frame to select a size and shape of the ROI, the frame including a plurality of subframes, the subframes being pivotally connected;
- adjusting positions of the subframes relative to the ROI to position a plurality of radiation detectors supported by the subframes at fixed viewing angles of the ROI, the radiation detectors generating radiation data indicating a location of gamma photons on each detector;
- determining a shape of the frames and viewing angles of the radiation detectors with sensors;
- collecting by at least one processor the radiation data from the radiation detectors and the determined viewing angles of the radiation detectors; and,
- reconstructing by the processor an image of the ROI from the received radiation data.

15. The method according to claim 14, wherein the reconfiguring further includes adding and/or removing subframes.

16. The method according to claim 14, wherein the subframes are configured in the shape of one of a circle, an ellipse, and a partial circle for the ROI.

17. The method according to claim 14, further including:
- removing the radiation detectors from another frame; and
- mounting the radiation detectors to a selected frame.

18. The method according to claim 14, wherein each radiation detector includes digital and/or analog silicon photomultipliers and/or semiconductor gamma detectors generating radiation data.

* * * * *